United States Patent [19]

Sampathkumar

[11] Patent Number: 4,990,329

[45] Date of Patent: Feb. 5, 1991

[54] COMPOSITION FOR TREATING ORAL DISEASES

[75] Inventor: Padmini Sampathkumar, Fairfield, Ohio

[73] Assignee: The Procter & Gamble Company, Cincinnati, Ohio

[21] Appl. No.: 266,316

[22] Filed: Nov. 3, 1988

Related U.S. Application Data

[60] Continuation of Ser. No. 942,471, Dec. 15, 1986, abandoned, which is a division of Ser. No. 738,103, May 24, 1985, Pat. No. 4,670,252.

[51] Int. Cl.$^5$ .................... A61K 7/29; A61K 7/18; A61K 7/16
[52] U.S. Cl. .................... 424/53; 424/49; 424/52; 514/900; 514/901; 514/902
[58] Field of Search .................... 424/49, 53, 52; 514/900–902, 714

[56] References Cited

U.S. PATENT DOCUMENTS

| | | | |
|---|---|---|---|
| 3,988,433 | 10/1976 | Benedict | 424/53 |
| 4,350,681 | 9/1982 | Fulton | 424/53 |
| 4,385,008 | 5/1983 | Hignett | 260/502 R |
| 4,403,994 | 9/1983 | Hignett | 8/111 |
| 4,483,781 | 11/1984 | Hartman | 252/174.12 |
| 4,490,269 | 12/1984 | Gallopo | 252/94 |
| 4,670,252 | 6/1987 | Stampathkumar | 424/53 |

FOREIGN PATENT DOCUMENTS

| | | |
|---|---|---|
| 0027693 | 4/1981 | European Pat. Off. . |
| 133354 | 2/1985 | European Pat. Off. . |
| 96525 | 12/1988 | European Pat. Off. . |
| 3133425A1 | 3/1983 | Fed. Rep. of Germany . |
| 1477691 | 6/1977 | United Kingdom . |
| 2137882A | 3/1983 | United Kingdom . |

OTHER PUBLICATIONS

Chemical Abstracts No. 67542e.

*Primary Examiner*—F. T. Moezie
*Attorney, Agent, or Firm*—Milton B. Graff, IV; Kim William Zerby; Steven J. Goldstein

[57] ABSTRACT

The invention relates to an oral hygiene composition for treating or preventing anaerobe infections in humans and lower animals.

14 Claims, No Drawings 4,990,329

COMPOSITION FOR TREATING ORAL DISEASES

TECHNICAL FIELD

This invention relates to a method for treating or preventing topically-treatable anaerobe infections, especially diseases of the oral cavity, such as gingivitis, periodontal disease, and acne, in humans or lower animals. This invention further relates to therapeutic rinses, especially mouth rinses, as well as toothpastes and gels, chewing gums, mouth sprays, lozenges, and sachets which are useful for treating or preventing topically-treatable anaerobe infections, especially diseases of the oral cavity, in humans or lower animals. In addition, the present invention relates to kits for making mouth rinses.

BACKGROUND OF THE INVENTION

Virtually all anaerobic infections arise endogenously. Anaerobic bacteria are a part of the normal flora of the skin. They also exist prevalently on all mucous membrane surfaces as indigenous flora. Given the proper circumstances and opportunity to penetrate tissues, anaerobes from the indigenous flora set up infections, such as gas gangrene, vulvovaginal abscess, chronic sinusitis, and Vincent's disease. While treatment with hyperbaric oxygen or hydrogen peroxide may be effective against certain anaerobe infections, there is a need for safe and effective methods of treating or preventing anaerobe infections generally.

Periodontal diseases are believed to involve anaerobic bacterial infections. Periodontal disease affects the periodontum, which is the investing and supporting tissues surrounding a tooth (i.e., the periodontal ligament, the gingiva, and the alveolar bone). Gingivitis and periodontitis are inflammatory disorders of the gingiva and the periodontal ligament, respectively. Gingivosis and periodontosis are more severe conditions involving degenerative disorders of the tissue. Combinations of inflammatory and degenerative conditions are termed periodontitis complex.

Periodontal disease is a major cause of tooth loss in adults. Tooth loss from periodontal disease is a significant problem beginning at age 35, but even by age 15 it is estimated that about 4 out of 5 persons already have gingivitis and 4 out of 10 have periodontitis.

While good oral hygiene, as achieved by brushing the teeth with a cleansing dentifrice, may help reduce the incidence of periodontal disease, it does not necessarily prevent or eliminate its occurrence. This is because microorganisms contribute to both the initiation and progress of periodontal disease. Thus, in order to prevent or treat periodontal disease, these microorganisms must be suppressed by some means other than simple mechanical scrubbing. Towards this end, there has been a great deal of research aimed at developing therapeutic dentifrices, mouthwashes, and methods of treating periodontal disease which are effective in suppressing these microorganisms.

It is the purpose of the present invention to provide a method for treating or preventing topically-treatable anaerobe infections, especially diseases of the oral cavity, in humans or lower animals by utilizing a monoperphthalic acid compound, or its pharmaceutically-acceptable salts or esters. Further, the present invention provides therapeutic rinses, especially mouth rinses, as well as toothpastes and gels, chewing gums, mouth sprays, lozenges, and sachets, containing a monoperphthalic acid compound, or its pharmaceutically-acceptable salts or esters, which are safe and effective in killing, and for a period of time suppressing the growth of, the microorganisms (especially anaerobic microorganisms) which cause topically-treatable anaerobe infections, especially diseases of the oral cavity, such as gingivitis, periodontal disease, and acne. In addition, the present invention relates to kits for making mouth rinses with limited concentrations of a monoperphthalic acid compound.

BACKGROUND REFERENCES

European patent application No. 27,693, published Apr. 29, 1981, filed by Interox Chemicals Limited, discloses the magnesium salts of peroxycarboxylic acids, including the magnesium salt of monoperphthalic acid, and processes for preparing these compounds. The compounds are used as bleaching agents in washing compositions.

European patent application No. 96,525, published Dec. 21, 1983, filed by Interox Chemicals Limited, discloses compositions containing magnesium salts of organic peroxy acid/carboxylate compounds, including magnesium monoperphthalate. These compositions are used for the cleansing and sanitization of reuseable diapers.

Great Britain patent application No. 2,137,882, published Oct. 17, 1984, filed by Interox Chemicals Limited, discloses disinfectants containing magnesium peroxycarboxylates, including magnesium monoperphthalate. These compositions are used for disinfecting/sterilizing hard surfaces such as toilets or drains, or equipment used in medical/veterinary or food processing environments.

U.S. Pat. No. 4,490,269, issued Dec. 25, 1984 to Gallopo, discloses cleansing compositions comprising an effervescent agent and a monoperphthalate, or an effervescent agent and a potassium monopersulfate and a monoperphthalate, as bleaching agents. These compositions are used to cleanse removable orthodontic appliances such as false teeth, dental plates and bridges.

European patent application No. 133,354, published Feb. 20, 1985, filed by Interox Chemicals Limited discloses compositions, generally in tablet form, containing a peroxygen compound (including monoperphthalate) and an effervescence generator. These compositions are dissolved in water to produce a bath in which to soak, and thereby cleanse, removable dentures.

U.S. Pat. No. 3,988,433, issued Oct. 26, 1976 to Benedict, and Great Britain Pat. No. 1,477,691, issued Oct. 19, 1977 to Jones et al., disclose compositions which contain alkyl and aryl peroxy acids. These compositions are used to remove stains from teeth.

U.S. Pat. No. 4,350,681, issued Sept. 21, 1982 to Fulton, discloses compositions containing benzoyl peroxide stabilized in an aqueous medium by the presence of glycerol. These compositions are used as toothpastes or body scrubs.

Merka et al., *Voenno-Med. Zh.*, Vol. 2, pp 46–50 (1967), investigates the disinfectant properties of several peroxide compounds, including monoperphthalic acid.

SUMMARY OF THE INVENTION

The present invention relates to a method of treating or preventing topically-treatable anaerobe infections, especially diseases of the oral cavity, such as gingivitis, periodontal disease, and acne, in humans or lower animals by topically applying to the infected tissue or the at-risk tissue, especially the tissue of the oral cavity, of the human or lower animal being treated, a safe and effective amount of a monoperphthalic acid compound having the general structure:

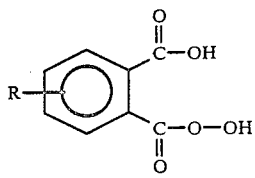

or its pharmaceutically-acceptable salts or esters, wherein R may be one or more substituents compatible with the peroxy acid functionality of the aromatic ring, preferred R being hydrogen.

The present invention further relates to toothpaste, mouth rinse, chewing gum, mouth spray, lozenge, and sachet compositions, as well as other therapeutic rinse compositions, which contain a safe and effective amount of a monoperphthalic acid compound, preferably magnesium monoperphthalic acid, and which are useful for treating or preventing topically-treatable anaerobe infections, especially diseases of the oral cavity, in humans or lower animals according to the methods of treatment of the present invention.

In addition, the present invention relates to a kit for making aqueous mouth rinse solutions according to the present invention which contain a monoperphthalic acid compound, preferably magnesium monoperphthalic acid, for treating or preventing diseases of the oral cavity in humans or lower animals according to the method of treatment of the present invention, said kit comprising (a) a concentrate of the monoperphthalic acid compound, preferably a concentrate of magnesium monoperphthalic acid, and (b) a means for facilitating the dilution of the concentrate with water to produce a mouth rinse solution which has from about 30 ppm to about 1200 ppm, preferably from about 60 ppm to about 300 ppm, of available oxygen generated by the monoperphthalic acid compound.

DETAILED DESCRIPTION OF THE INVENTION

The present invention relates to a method of treating or preventing topically-treatable anaerobe infections, especially diseases of the oral cavity (e.g. periodontal disease), in humans or lower animals by topically applying to the tissue, especially the tissue of the oral cavity, of the human or lower animal, a safe and effective amount of a singlet oxygen generating organic peroxy acid compound. By "singlet oxygen generating organic peroxy acid compound" as used herein is meant an organic acyl peroxide compound (e.g., an organic molecule which has at least one —CO₃H substituent) by itself, or in combination with hydrogen peroxide, whose oxidative ability is inhibited by greater than about 30% by a well-known singlet oxygen quencher (e.g. tertiary aliphatic amines such as 1,4-diazabicyclo[2.2.2.]octane ("DABCO")) when the quencher is added at the same molar concentration as the organic acyl peroxide in solution. This inhibition can be monitored in two ways: (a) by monitoring the oxidation by the organic peroxy acid compound of a reactive substrate such as 1,3-diphenylisobenzofuran in the presence and absence of equimolar amounts of the singlet oxygen quencher, especially DABCO; and (b) by monitoring the antibacterial activity towards anaerobic bacteria (especially Fusobacterium such as F.nucleatum) of the organic peroxy acid compound in the presence and absence of equimolar amounts of the singlet oxygen quencher, especially DABCO. Organic peroxy acid compounds whose activity, as monitored by (a) or (b) above are inhibited to an extent greater than about 30% by the singlet oxygen quencher (e.g., DABCO) are considered for the purposes of this invention to be singlet oxygen generating organic peroxy acid compounds.

The present invention further relates to a method of treating or preventing topically-treatable anaerobe infections, especially diseases of the oral cavity, (e.g., gingivitis; periodontal disease; acne), in humans or lower animals by topically applying to the infected tissue or the at-risk tissue, especially the tissue of the oral cavity, of the human or lower animal being treated, a safe and effective amount of a substituted monoperphthalic acid compound having the general structure:

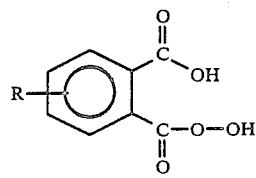

or its pharmaceutically acceptable salts or esters, wherein R may be one or more substituents compatible with the peroxy acid functionality of the aromatic ring.

By "substituents compatible with the peroxy acid functionality of the aromatic ring", as used herein, is meant substituents on the ring which do not react with peroxy acids thereby reducing the stability and effectiveness of the compounds to treat diseases of the oral cavity. Nonlimiting examples of R groups include hydrogen, substituted and unsubstituted saturated alkyl having from 1 to about 20 carbon atoms (e.g., methyl, ethyl), substituted and unsubstituted aryl (e.g., phenyl, naphthyl), substituted and unsubstituted benzyl, chloro, fluoro, nitro, sulphonate, trifluoromethyl, trialkylammonium (e.g., trimethylammonium; triethylammonium), cyano, carboxy, carboxylate (e.g.,—OCOCH₃), percarboxylate (e.g.,—CO₃H), and alkoxy (e.g., methoxy, ethoxy). Preferred R groups are hydrogen, saturated alkyl having from 1 to about 20 carbon atoms, aryl, benzyl, chloro, fluoro, carboxy, and alkoxy. Particularly preferred for use in the above method for treating or preventing diseases of the oral cavity is monoperphthalic acid (i.e., R=H), or its pharmaceutically-acceptable salts or esters. R may also be an iodo, bromo, substituted or unsubstituted amino, or amido group, but such groups are generally not desirable since they can react with peroxy acid groups. Selection of substituents compatible with the peroxy acid functionality of the aromatic ring can easily be made by one skilled in the art.

The present invention is the result of the surprising discovery that monoperphthalate, particularly the magnesium salt of monoperphthalic acid, is a very effective antimicrobial agent against anaerobic bacteria, especially the anaerobic bacteria found in the mouth. This antibacterial activity is selective for anaerobic bacteria, especially at lower monoperphthalate concentrations. The efficacy of the antibacterial activity in vitro versus several types of bacteria is set forth in Table I. As can be seen from Table I, low concentrations of magnesium monoperphthalate are very effective in killing fastidious anaerobic bacteria which are implicated in gingivitis, periodontitis and other serious anaerobe infections; and at somewhat higher concentrations in also killing facultative anaerobic bacteria such as the caries-causing *S. mutans*.

days only (2 rinses per day). At the end of this period, following only a total of 3 rinses, there was a dramatic decrease (greater than 4 log reduction) in the number of anaerobes in the plaque of the subjects treated with the magnesium monoperphthalic acid, while there was no significant decrease in the number of anaerobes in the plaque of subjects rinsing with the placebo. The greater

TABLE I

| | In Vitro Efficacy of Magnesium Monoperphthalate | | | | | |
|---|---|---|---|---|---|---|
| | 0% Mg monoperphthalate | | 0.05% Mg monoperphthalate | | 0.5% Mg monoperphthalate | |
| Bacterial Species | # bacteria (logs)[a] | (% Kill)[a] | # bacteria (logs)[a] | (% Kill)[a] | # bacteria (logs)[a] | (% Kill)[a] |
| I. *Fastidious anaerobes:* | | | | | | |
| *F. nucleatum*[b,d] | 7 | (0%) | 0 | (100%) | 0 | (100%) |
| *N. sicca*[b] | 7 | (0%) | 0 | (100%) | 0 | (100%) |
| *V. parvula*[b] | 7 | (0%) | 0 | (100%) | 0 | (100%) |
| *B. intermedius*[b,d] | 7 | (0%) | 0 | (100%) | 0 | (100%) |
| *C. pasteurianum*[d] | 7 | (0%) | 0 | (100%) | 0 | (100%) |
| *C. perfringens*[d,e] | 7 | (0%) | 0 | (100%) | 0 | (100%) |
| *B. fragilis*[d,e] | 7 | (0%) | 0 | (100%) | 0 | (100%) |
| II. *Facultative anaerobes:* | | | | | | |
| *S. mutans*[c] | 6 | (0%) | 4 | (99.0%) | 0 | (100%) |
| *A. naeslundii*[c] | 7 | (0%) | 4 | (99.9%) | 0 | (100%) |
| *A. israelii*[c] | 7 | (0%) | 4 | (99.9%) | 0 | (100%) |
| III. *Aerobe* | | | | | | |
| *P. aeruginosa* | 7 | (0%) | 7 | (0%) | 3 | (99.99%) |

[a] after 15 minutes of exposure; one log reduction is a 10X reduction in the number of anaerobes (e.g., reduction from 7 logs to 0 logs reduces the number of live bacteria from 10 million to zero)
[b] anaerobes implicated in gingivitis and periodontitis
[c] anaerobe implicated in caries
[d] anaerobes which are members of groups of organisms which account for a majority of anaerobic isolates from clinical infections.
[e] a member of a group of organisms that are very virulent The present invention is also the result of the discovery of surprising properties of monoperphthalic acid compounds, particularly the magnesium salt of monoperphthalic acid, which are believed to make this specific class of compounds very desirable and effective for treating anaerobe infections, especially diseases of the oral cavity. Particularly surprising is magnesium monoperphthalate's apparently highly effective ability in vivo to penetrate through the layer of mucous, tissue and aerobic bacteria to reach and kill the anaerobic bacteria underneath. Further, magnesium monoperphthalate is relatively stable to enzymatic decomposition, especially to the enzymes found in the oral cavity, thereby allowing an effective amount of the compound to exert its antibacterial activity in vivo. Also in vivo magnesium monoperphthalate not only preferentially kills the anaerobic bacteria, but also suppresses regrowth of these bacteria.

than 4 log reduction observed in the subjects treated with the magnesium monoperphthalic acid means that while there were 20 million ($2 \times 10^7$) anaerobes on the surface of the plaque before treatment (the baseline), at the end of just three 30 second rinses the number of anaerobes fell to only 2,000 ($2 \times 10^3$). This is a highly significant ($p < 0.001$) decrease, and provides convincing evidence of the potency of this magnesium monoperphthalic acid solution. Importantly, this highly significant reduction in the number of anaerobes in plaque is maintained for longer than 4 hours following the final rinse with the active, thus suppressing the regrowth of anaerobic bacteria and providing significant antibacterial benefit between exposures to the active. It is expected that prolonged use of the active (for a period of about 3 weeks, twice a day) would result in a decrease of about 3 logs in the number of aerobes in plaque, thereby further providing anti-caries benefits.

TABLE II

| Effect of Magnesium Monoperphthalate Mouthrinse on Plaque Bacteria | | | | |
|---|---|---|---|---|
| | Difference (in Log - Colony Forming Units from start of treatment)[a] | | | |
| | 0 hrs. after final rinse | | 4 hrs. after final rinse | |
| Class of Bacteria | active | placebo | active | placebo |
| aerobes | 0.3 ± 0.14 | 0.09 ± 0.18 | 0.03 ± 0.15 | 0.1 ± 0.18 |
| anaerobes | 4.17 ± 0.4[b] | 0.84 ± 0.55 | 3.03 ± 0.44[b] | 0.36 ± 0.43 |

[a] decrease in log units per tooth; one log unit decrease is a 10 × decrease in the number of bacteria
[b] statistically significant difference ($p < 0.001$) from baseline.

Table II demonstrates the above stated efficacy, which is very rapid and highly preferential for anaerobic bacteria. Table II gives some of the results obtained from a study in which 30 human subjects were divided randomly into two groups and each group rinsed for 30 seconds with either a placebo or a 0.5% solution of magnesium monoperphthalic acid for one and one half The above noted properties and selectivity for anaerobes is desirable for treating anaerobe infections, especially diseases of the oral cavity, such as acne, gingivitis, and periodontal disease. For the treatment of anaerobe infections generally, selectivity of the method for anaerobes is desirable because it may be detrimental to the tissue to kill all the normal flora of the tissue. Broad spectrum antibacterials kill all the normal flora, and this creates the potential for diseases that the normal flora may act to prevent, such as yeast infections. Thus, the selectivity of the method of treatment of the present invention allows part of the normal flora to survive while killing the pathogenic anaerobes contained therein.

For a method of treating diseases of the oral cavity, selectivity in killing anaerobes is particularly desirable. First, as noted above, broad spectrum antibacterials kill all the normal flora of the mouth, leaving the oral cavity open to diseases the normal flora may act to prevent, such as yeast infections. Second, broad spectrum antibacterials, such as chlorhexidine, cause tooth staining which is believed to be a direct result of killing all bacteria in the mouth. Thus, the selectivity of monoperphthalic acid compounds (especially the selectivity at concentrations of less than about 1200 ppm of active oxygen, and preferably less than about 300 ppm active oxygen, particularly the selectivity of magnesium monoperphthalic acid, is believed to result in a non-staining method for treating diseases of the oral cavity because it does not kill all the bacteria of the oral cavity. In addition, since these monoperphthalate compounds are also weak bleaches, there may be stain removal benefits due to the bleaching activity.

Another important feature of the methods of treatment of the present invention is that these treatments are believed to be safe for chronic treatment of topically-treatable anaerobe infections, especially diseases of the oral cavity. Unlike the diacyl peroxides, like benzoyl peroxide, which decompose by a free radical mechanism, the aqueous decomposition of monoperphthalate does not involve the generation of significant free radicals. This property is especially relevant for safety reasons, since free radicals are known to have detrimental effects on tissues and can lead to severe inflammatory responses. Long-term treatment with free radical generators is therefore not desirable. The absence of free radical mechanisms for monoperphthalate strongly indicates that long-term treatment with monoperphthalate should be safe and pose no significant health hazards.

The above results are particularly interesting in light of the fact that other closely-related aromatic peroxy acid compounds, in particular diperisophthalic acid (which differs from monoperphthalic acid only in that there are two peroxy acid groups which are meta rather than a carboxylate ortho to a peroxy acid), demonstrate no significant efficacy in treating gingivitis. It is believed that the above properties of monoperphthalate, especially its effectiveness in treating or preventing gingivitis, periodonitis, and periodontal disease, are unique to this specific class of aromatic peroxy acids. While not intending to be limited by theory, it appears that the electronic configuration and/or steric factors present in monoperphthalate compounds, which result from the interaction of the ortho substituted carboxy and monoperoxy acid groups, lead to unique properties which are particularly well-suited for the methods of treatment of the present invention, particularly for treating or preventing diseases of the oral cavity.

By "pharmaceutically-acceptable salts or esters", as used herein, is meant esters and salts of the substituted or unsubstituted monoperphthalic acid compounds which have the same general antibacterial properties as the preferred magnesium salt of monoperphthalic acid, and which are acceptable from a toxicity viewpoint. Nonlimiting examples of pharmaceutically-acceptable salts include alkali metal (e.g., sodium, potassium), alkaline earth metal (e.g., calcium, magnesium), non-toxic heavy metal, and trialkyl ammonium (e.g., trimethylammonium). Preferred compounds for treating or preventing diseases of the oral cavity are pharmaceutically-acceptable salts of the substituted or unsubstituted monoperphthalic acid compounds, with the pharmaceutically-acceptable salts of divalent cations more preferred (e.g., magnesium, calcium), and the magnesium salt being the most preferred.

Most preferred for use in the above method of treating or preventing surface tissue infections caused by or involving anaerobic bacteria, and particularly preferred for diseases of the oral cavity, is the magnesium salt of monoperphthalic acid. This magnesium salt is the salt of the carboxylic acid group only, having the formula:

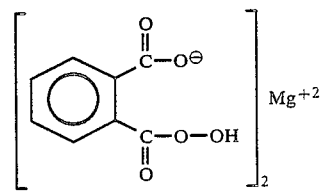

as disclosed in European patent application No. 27,693, published Apr. 29, 1981, filed by Interox Chemicals, Ltd., the disclosures of which are incorporated herein by reference. This compound is a hydrate when in its solid form.

Synthesis of substituted and unsubstituted monoperphthalic acid compounds can be achieved by those skilled in the art using methods disclosed in, for example, European patent application No. 27,693, published Apr. 29, 1981, filed by Interox Chemicals Limited; European patent application 66,992, to Interox Chemicals Limited; U.S. Pat. No. 3,075,921, to Brockelhurst et al.; "Organic Peroxides", Daniel Swern, Editor, published 1970 by John Wiley & Sons, Inc.; and in British patent specification No. 1,378,671; the disclosures of all of which being incorporated herein by reference. Synthesis of the magnesium salt of monoperphthalic acid is disclosed in the European patent application No. 27,693, cited above. This compound is also commercially available from Interox Chemicals Limited.

By "topically-treatable anaerobe infections", as used herein, is meant tissue infections which are caused by or involve anaerobic bacteria, and may be treated by topical application. Generally, the tissues that may be treated by topical application are external mucous membranes and mucocutaneous orifices. Non-limiting examples of anaerobe infections that may be treated by topical application include anaerobe infections of the skin or soft tissue (e.g., acne, dandruff, gas gangrene (anaerobic myonecrosis), gas-forming cellulitis, perirectal abscess, breast abscess, dermatological lesions, wound infections, bovine mastitis), the vagina (e.g., vulvovaginal abscess), the uterus (e.g., uterine infections), urinary tract infections, the eyes (e.g., conjunctivitis, lid infections), the ears (e.g., otitis media, mastoiditis), the sinuses (e.g., sinusitis), and diseases of the oral cavity (e.g., Vincent's disease, periodontal disease). Not included are internal anaerobe infections that require enteral or systemic treatment methods to deliver the active to the infected tissue, such as abdominal infections, cardiovascular infections, central nervous system infections, lung infections, stomach and intestinal infections, and bone and joint infections. Specific anaerobe infections are more fully disclosed in Finegold, *Anaerobic Bacteria in Human Diseases*, (Academic Press, Inc., NY, 1977), and in *Anaerobic Bacteria: Role in Disease* (published by Charles C. Thomas, Springfield, Ill.; Albert Balows, et al., editors; 1974), the disclosures of both of which are incorporated herein by reference.

By "diseases of the oral cavity", as used herein, is meant diseases which are initiated and/or perpetuated by bacteria in the oral cavity, especially anaerobic bacteria, and includes such diseases as, for example, periodontal disease, gingivitis, periodontitis, gingivosis, periodontosis, periodontitis complex, and other inflammatory and/or degenerative conditions of the tissues within the oral cavity, plus caries, Vincent's disease, trench mouth, and malodor. Also specifically included are dentoalveolar infectious, dental abscesses (e.g., cellulitis of the jaw; osteomyelitis of the jaw), acute necrotizing ulcerative gingivitis (i.e., Vincent's infection), infectious stomatitis (i.e., acute inflammation of the buccal mucosa), and Noma (i.e., gangrenous stomatitis or cancrum oris). Oral and dental infections are more fully disclosed in Finegold, *Anaerobic Bacteria in Human Diseases*, chapter 4, pp 78–104, and chapter 6, pp 115–154 (Academic Press, Inc., NY, 1977), the disclosures of which are incorporated herein by reference. The method of treatment of the present invention is particularly effective for treating or preventing periodontal disease, gingivitis and/or periodontitis.

By "safe and effective amount" as used herein is meant an amount of a monoperphthalic acid compound, or its pharmaceutically-acceptable salt or ester, high enough to significantly positively modify the infection to be treated, but low enough to avoid serious side effects (at a reasonable benefit/risk ratio), within the scope of sound medical judgment. The safe and effective amount of a monoperphthalic acid compound or its pharmaceutically-acceptable salt or ester will vary with the particular infection (e.g., disease of the oral cavity) being treated, the age and physical condition of the patient being treated, the severity of the infection, the duration of treatment, the nature of concurrent therapy, the specific form (i.e., acid, salt, and/or ester) of the monoperphthalic acid employed, and the particular vehicle from which the monoperphthalic acid is applied.

It is preferred for the method of treatment of the present invention that the safe and effective amount of monoperphthalic acid compound which is taken into the oral cavity (based on equivalents of peroxide units per compound) be from about $5 \times 10^{-6}$ moles to about $5 \times 10^{-3}$ moles, more preferred being from about $5 \times 10^{-6}$ moles to about $2 \times 10^{-3}$ moles, with from about $5 \times 10^{-5}$ moles to about $5 \times 10^{-4}$ moles most preferred. For the preferred magnesium salt of monoperphthalic acid, this is equivalent to from about 1 mg to about 1000 mg, with more preferred being from about 1 mg to about 400 mg, and from about 10 mg to about 100 mg most preferred.

It is further preferred that the concentration of the monoperphthalic acid compound in the medium contacting the tissue (e.g., toothpaste diluted with water and saliva during brushing constitutes the medium) be such that the concentration of the active oxygen ("A.O.") in the medium that contacts the tissue (gingival tissue or otherwise) be in the range of from about 30 ppm to about 3500 ppm, with from about 30 ppm to about 1200 ppm preferred, and 60 ppm to about 300 ppm most preferred. In order to avoid the potential for teeth staining thought to be associated with broad spectrum antimicrobials, the A.O. concentration range (generated by the monoperphthalic acid compound) of from about 30 ppm to about 1200 ppm, and especially the range of from about 60 ppm to about 300 ppm, are preferred for treating or preventing diseases of the oral cavity, especially when chronic treatment is required or desired, due to the higher selectivity for anaerobes vs. aerobes at these concentrations. If anti-caries benefits are particularly desired, it is preferred that the A.O. be above about 60 ppm. For the preferred magnesium salt of monoperphthalic acid, the above ranges are equivalent to from about 0.05% (wt/v) to about 5% (wt/v), with from about 0.05% to about 2% more preferred, and from about 0.1% to about 0.5% most preferred.

The safe and effective amount of the monoperphthalic acid compound may be topically applied to the gingival tissue of the oral cavity in several conventional ways. For example, the gingival tissue may be rinsed with a solution (e.g., mouth rinse, mouth spray) containing the monoperphthalic acid compound; or if the monoperphthalic acid compound is included in a dentifrice (e.g., toothpaste, gel or toothpowder), the gingival tissue are bathed in the liquid and/or lather generated by brushing the teeth. Other non-limiting examples include applying a gel or paste which contains the monoperphthalic acid compound directly to the gingival tissue; chewing a gum or chewable tablets that contain the monoperphthalic acid compound; and sucking on a lozenge or sachet which contains the monoperphthalic acid compound. Preferred methods of applying the monoperphthalic acid compound to the gingival tissue are via rinsing with a mouth rinse solution, and via brushing with a dentifrice. Other methods of topically applying the monoperphthalic acid compound to the gingival tissue are apparent to those skilled in the art.

The safe and effective amount of the monoperphthalic acid compound topically applied to the skin, e.g., for treating or preventing acne, may be done in several ways, e.g., as a body scrub, rinse, cream, gel, or lotion. For treating or preventing vaginal infections, several ways of topically applying the safe and effective amount of the monoperphthalic acid compound to the tissue of the vagina may include, e.g., a vaginal douche solution, cream, foam or gel. The preferred method of topically applying the monoperphthalic acid compound to infected tissue is via a rinse, cream, or lotion. Other methods of topical application are apparent to those skilled in the art.

It is preferred for the method of treatment of the present invention that the treatment be done in such a way that the pH, particularly the pH of the oral cavity, during treatment is maintained at a pH of from about 5 to about 8, more preferably from about 7.0 to about 7.5. One way to do this is by buffering (e.g., the oral cavity) during treatment. Non-limiting examples of pharmaceutically-acceptable buffers include citrate, citrate/bicarbonate and phosphate buffers. It is also preferred that in the method of treating diseases of the oral cavity of the present invention the monoperphthalic acid compound not be intentionally ingested.

The concentration of the monoperphthalic acid compound in the composition used in the method of treating diseases of the oral cavity of the present invention depends on the type of composition (e.g., toothpaste, mouth rinse, lozenge) used to apply the monoperphthalic acid compound to the gingival tissue, due to differences in efficiency of the compositions to contact the tissue, and due also to the amount of the composition generally used.

It is preferred that the mouth rinse to be taken into the oral cavity have a concentration of monoperphthalic acid compound in the range of from about 0.05% (w/v) to about 5% (w/v) (this introduces from about 1 mg to about 1000 mg of magnesium monoperphthalate into the oral cavity per average 15 ml rinse), with from about 0.05% to about 2% more preferred, and from about 0.1% to about 0.5% most preferred. Mouth sprays preferably have monoperphthalic acid compound concentrations of from about 0.1% (w/v) to about 25% (w/v), with from about 0.5% to about 10% most preferred. For dentifrices, the concentration of monoperphthalic acid compound is in the range of from about 0.1% to about 50% (this introduces from about 1 mg to about 500 mg of magnesium monoperphthalic acid per use, for example, for an average 1 ml application of dentifrice), with from about 1% to about 35% preferred. Chewable tablets, chewing gums, lozenges, and sachets are generally formulated into compositions of individual unit size preferably containing from about 20 mg to about 500 mg of monoperphthalic acid compound per unit used in the oral cavity (i.e. per tablet, stick of gum, lozenge, etc.).

For treating tissue other than the gingival tissue, it is preferred that rinses (e.g., vaginal douche; nasal spray), creams, and lotions have a concentration of monoperphthalic acid compound in the range of from about 0.05% to about 5%, with from about 0.05% to about 2% more preferred, and from about 0.1% to about 0.5% most preferred. Concentrated compositions that will be diluted by water during use, e.g., body scrub or soak, preferably contain from about 1% to about 50% of the monoperphthalic acid compound.

For the method of treating diseases of the oral cavity of the present invention, the safe and effective amount of monoperphthalic acid compound is preferably applied to the gingival tissue for at least about 30 seconds from about one to about six times daily, with two times daily preferred. The duration of treatment is preferably from about 3 weeks to about 3 months, but may be shorter or longer depending on the severity of the oral disease being treated, the particular delivery form utilized and the patient's response to treatment. Similar treatment regimens are utilized for treating other topically-treatable anaerobe infections, e.g., using a body scrub containing the safe and effective amount of monoperphthalic acid compound to scrub the tissue infected with acne for at least about 30 seconds from about one to about six times daily; using a shampoo containing the safe and effective amount of monoperphthalic acid compound to wash the tissue infected with dandruff for at least about 30 seconds from about one to about six times daily; and using a vaginal douche containing the safe and effective amount of monoperphthalic acid compound to rinse the infected vaginal tissue for at least about 30 seconds from about one to about six times daily.

The present invention further relates to compositions for use in the methods of treatments according to the present invention. In particular, the present invention further relates to rinses, especially mouth rinses, as well as toothpastes (including gels), mouth sprays, chewing gums, lozenges, and sachets comprising: (1) a safe and effective amount of a monoperphthalic acid compound, or its pharmaceutically-acceptable salts or esters, and (2) a carrier acceptable for oral administration. The monoperphthalic acid compounds which may be used in these compositions are the same as described above (preferred being the unsubstituted aromatic ring (i.e., R=H)), with again the pharmaceutically-acceptable salt form preferred, the pharmaceutically-acceptable divalent salt form more preferred. Most preferred is the magnesium salt of monoperphthalic acid. These compositions are taken into the oral cavity, or topically applied to other infected tissue, and retained there in such a way and for such time as to be effective for treating or preventing diseases of the oral cavity and other topically-treatable anaerobe infections according to the method of the present invention. It is preferred that these compositions not be intentionally ingested. Toothpastes (including gels) and mouth rinses are preferred.

The rinses, especially the mouth rinses, of the present invention have a concentration (on a weight to volume basis) of monoperphthalic acid compound in the range of from about 0.05% to about 5%, preferred being from about 0.05% to about 2%, with from about 0.1% to about 0.5% most preferred. Mouth sprays of the present invention have a concentration of monoperphthalic acid compound of from about 0.1% to about 25%, with from about 0.5% to about 10% preferred. Toothpastes (including gels) of the present invention preferably comprise from about 0.1% to about 50% of monoperphthalic acid compound, with from about 1% to about 35% most preferred. Chewing gums, lozenges, and sachets of the present invention preferably comprise from about $1 \times 10^{-4}$ moles to about $2.5 \times 10^{-3}$ moles of monoperphthalic acid compound (from about 20 mg to about 500 mg of magnesium monoperhthalate) per unit used in the oral cavity, with from about $2.5 \times 10^{-4}$ moles to about $1.75 \times 10^{-3}$ moles more preferred (from about 50 mg to about 350 mg of magnesium monoperphthalate).

Creams and lotions for treating or preventing topically-treatable anaerobe infections other than diseases of the oral cavity, such as acne, have a concentration of monoperphthalic acid compound in the range of from about 0.05% to about 25%, with from about 0.05% to about 5% preferred, and from about 0.1% to about 1% most preferred.

The compositions of the present invention are very effective in killing, and for a period of time preventing the regrowth of anaerobic bacteria. Thus, they are useful for treating or preventing topically-treatable anaerobe infections, especially diseases of the oral cavity, in humans or lower animals. In addition, use of these compositions (especially at the lower concentrations) to treat or prevent diseases of the oral cavity will not stain the teeth, unlike the broad spectrum antimicrobials which have been suggested for use in treating periodontal disease (e.g., chlorhexidine).

By "carrier", as used herein, is meant one or more compatible solid or liquid filler diluents or encapsulating substances which are suitable for oral administration. By "compatible", as used herein, is meant that the components of the composition are capable of being comingled without interaction in a manner which would substantially reduce the composition's efficacy for treating or preventing topically-treatable anaerobe infections, especially diseases of the oral cavity, according to the method of the present invention. It is preferred that the carrier be buffered, or contain from 0% to about 50% of a buffer, capable of maintaining the pH of the oral cavity during use from about pH=5 to about pH=8, more preferred being pH from about 7.0 to about 7.5. Non-limiting examples of buffers include citrate, citrate/bicarbonate and phosphate buffers.

The carriers of the present invention can include the usual and conventional components of toothpastes (including gels), mouth rinses, mouth sprays, chewing gums, lozenges, and sachets as more fully described hereinafter. Generally, however, the carriers are limited to materials which are free of hydroxyl groups and normally also to materials which do not contain reactive sites, such as for example amino, amido, iodo, bromo, and sulfhydryl groups, and unsaturated, imino, and thioether linkages when the composition of the present invention is to be stored for any appreciable period of time. Thus, it is preferred that the monoperphthalic acid compound be substantially anhydrous until just prior to use, for example, preparing a mouth rinse solution just prior to use by dissolving substantially anhydrous concentrate of monoperphthalic acid compound in water to the necessary concentration for use in the method of treatment of the present invention.

It is contemplated, however, that even reactive carriers may be contained in the compositions of the present invention when the reactive carrier is stored separately from the monoperphthalic acid compounds and the product is used immediately after preparation. For example, toothpaste compositions conventionally contain abrasive materials, sudsing agents, binders, humectants, flavoring and sweetening agents. Most of these cannot be stored with the monoperphthalic acid compound. Therefore, toothpastes of the present invention will normally be two component compositions in separate containers or chambers, to be combined just before use. Other compatible additives and actives (e.g., fluoride) may be included in the compositions of the present invention.

The choice of a carrier to be used is basically determined by the way the composition is to be introduced into the oral cavity. If a toothpaste (including gels) is to be used, then a "toothpaste carrier" is chosen as disclosed in, e.g., U.S. Pat. No. 3,988,433, to Benedict, the disclosure of which is incorporated herein by reference (e.g., abrasive materials, sudsing agents, binders, humectants, flavoring and sweetening agents, etc.), or if a mouth rinse is to be used, then a "mouth rinse carrier" is chosen, also as disclosed in, e.g., U.S. Pat. No. 3,988,433 to Benedict (e.g., water, flavoring and sweetening agents, possibly an organic solvent such as ethanol, etc.). Generally, on a weight basis, mouthwashes comprise 5% to 60% (preferably 10% to 25%) ethanol, 0% to 20% (preferably 5% to 20%) of a humectant, 0% to 2% (preferably 0.01% to 0.15%) emusifying agent, 0% to 0.5% (preferably 0.005% to 0.06%) sweetening agent such as saccharin, 0% to 0.3% (preferably 0.03% to 0.3%) flavoring agent, and the balance water. Similarly, if a mouth spray is to be used, then a "mouth spray carrier" is chosen or if a lozenge is to be used, then a "lozenge carrier" is chosen (e.g., a candy base), candy bases being disclosed in, e.g., U.S. Pat. No. 4,472,373, to Ryan, and in U.S. Pat. No. 4,083,955, to Grabenstetter et al., both of which being incorporated herein by reference; if a chewing gum is to be used, then a "chewing gum carrier" is chosen, as disclosed in, e.g., U.S. Pat. No. 4,472,373 to Ryan, and in U.S. Pat. No. 4,083,955, to Grabenstetter et al., both of which being incorporated herein by reference (e.g., gum base, flavoring and sweetening agents); and if a sachet is to be used, then a "sachet carrier" is chosen (e.g., sachet bag, flavoring and sweetening agents). Carriers suitable for the preparation of compositions of the present invention are well known in the art. Their selection will depend on secondary considerations like taste, cost, shelf stability, which are not critical for the purpose of the present invention, and can be made without difficulty by a person skilled in the art.

Types of carriers which may be included in compositions of the present invention, along with specific non-limiting examples, are:

A. Abrasives

Abrasives normally are added only to dilute compositions intended for immediate use since many abrasives tend to make the peroxyacids unstable. Abrasives include dicalcium orthophosphate, calcium carbonate, beta-phase calcium pyrophosphate, prepared, for example, in accordance with the teachings of Schweizer, U.S. Pat. No. 3,112,247, granted Nov. 26, 1963, particulate thermosetting polymerized resins, e.g., as described by Cooley et al. in U.S. Pat. No. 3,070,510, granted Dec. 25, 1962 (e.g., melamines, phenolics, ureas, melamine-ureas, melamine formaldehydes, urea formaldehydes, melamine-urea formaldehydes, cross-linked epoxides and cross-linked polyesters), alumina, silica xerogels of the type disclosed in the abandoned application of Briner et al., Ser. No. 329,782, filed Feb. 9, 1973, and other phosphate and silica abrasives such as insoluble sodium metaphosphate. Mixtures of abrasives can also be used. The total amount of abrasive in the toothpastes of this invention can range from 0.5% to 95% by weight of the toothpaste. Preferably, toothpastes contain from about 20% to about 60% by weight of abrasive. Abrasive particle size preferably ranges from about 1 micron to about 30 microns.

B. Sudsing Agents:

Suitable sudsing agents are those which are reasonably stable and form foam throughout a wide pH range, preferably nonsoap anionic organic synthetic detergents which are relatively unreactive with the peroxyacids of this invention. Examples of such agents are water-soluble salts of alkyl sulfate having from 10 to 18 carbon atoms in the alkyl radical, such as sodium lauryl sulfate. Other somewhat more reactive detergents include water-soluble salts of sulfonated monoglycerides of fatty acids having from 10 to 18 carbon atoms, such as sodium monoglyceride sulfonates; salts of $C_{10}$-$C_{18}$ fatty acid amides of taurine, such as sodium N-methyl-N-palmitoyl tauride; salts of $C_{10}$-$C_{18}$ fatty acid esters of isethionic acid; and substantially saturated aliphatic acyl amides of saturated monoaminocarboxylic acids having 2 to 6 carbon atoms and in which the acyl radical contains 12 to 16 carbon atoms, such as sodium N-lauroyl sarcoside. Mixtures of two or more sudsing agents can be used. Other suitable sudsing agents include the nonionic, cationic, zwitterionic and amphoteric nonsoap organic synthetic detergents.

The nonionic synthetic detergents which can be used with the oral compositions of the present invention should not be part of concentrated compositions which are to be stored for long periods of time which contain the peroxyacids when the nonionic detergents contain reactive hydroxyl groups. Nonionic synthetic detergents may be broadly defined as compounds produced by the condensation of alkylene oxide groups (hydrophilic in nature) with an organic hydrophobic compound which may be aliphatic or alkyl-aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

For example, a well-known class of nonionic synthetic detergent is made available on the market under the trade name of "Pluronic." These compounds are formed by condensing ethylene oxide with a hydrophobic base formed by the condensation of propylene oxide with propylene glycol. The hydrophobic portion of the molecule which, of course, exhibits water insolubility, has a molecular weight of from about 900 to about 5,000. The addition of polyoxyethylene radicals to this hydrophobic portion tends to increase the water solubility of the molecule as a whole and the liquid character of the products is retained up to the point where polyoxyethylene content is about 50% of the total weight of the condensation product.

Other suitable sudsing agents are disclosed in U.S. Pat. No. 3,988,433, to Benedict, the disclosures of which are incorporated herein by reference.

The sudsing agent can be present in the dentifrice compositions of this invention in an amount from 0% to about 20%, preferably from about 0.5% to about 10%, more preferably from about 1% to about 5%, by weight of the total compositions.

C. Fluoride:

One can also include a water-soluble fluoride compound in the compositions of this invention in an amount of from 0% to about 10%, preferably in an amount to give a fluoride concentration of from about 0.0025% to about 5%, more preferably from about 0.005% to about 2.0%, to provide additional anticaries effectiveness. Preferred fluorides are sodium, indium, and stannous fluorides, and sodium monofluorophosphate. Suitable fluorides are disclosed in U.S. Pat. No. 3,535,421, which is incorporated herein by reference.

D. Thickening Agents:

In preparing toothpastes or gels, it is necessary to add some thickening material to provide a desirable consistency. However, almost all thickening agents, except polymeric polyester compounds, e.g., polyethylene or polypropylene oxide (M.W. 300 to 1,000,000), capped with alkyl or acyl groups containing 1 to about 18 carbon atoms will react with the peroxyacids. When the peroxyacids are formulated separately, preferred thickening agents are hydroxyethyl cellulose and water-soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0% to about 50%, preferably from about 0.5% to about 5.0% by weight of the total toothpaste or gel composition can be used. Higher concentrations can be used for chewing gums, lozenges and sachets.

E. Humectants:

It is also desirable to include some humectant material in a toothpaste or gel to keep it from hardening. Suitable humectants include glycerine, sorbitol, and other edible polyhydric alcohols. The humectant can comprise up to about 70%, preferably up to about 36% by weight of the toothpaste or gel composition. Alternatively, a composition can contain up to about 36% of a paraffin oil.

F. Flavoring and Sweetening Agents:

Suitable flavoring agents include oil of wintergreen, oil of peppermint, oil of spearmint, oil of sassafras, and oil of clove. Sweetening agents which can be used include saccharin, dextrose and levulose. A composition preferably contains from about 0.1% to about 10% of those agents. A composition also preferably contains a coloring agent in an amount from 0% to about 0.5%.

In a preferred embodiment, because of its reactivity, the monoperphthalic acid compound will be formulated into a composition consisting essentially of an inert organic or inorganic carrier selected for its limited reactivity with the oxidizing material. The primary function of the inert material is to support the peroxyacid and other desired adjuncts in the proper concentrations, either in a single composition or as part of a two-component composition.

The organic carrier can be either a liquid or a soft wax, preferably a liquid. As used herein, "saturated" is intended to include compounds containing aryl as well as saturated alkyl moieties. "Polyoxyalkylene" as used herein includes ethoxylated and propoxylated materials.

The organic carrier can desirably be a saturated nonionic synthetic detergent of the ethoxylated nonionic type capped with an alkyl or acyl group to eliminate the reactive hydroxy group. Nonionic synthetic detergents can be broadly defined as compounds produced by the condensation of alkylene oxide groups (hydrophilic in nature) with an organic hydrophobic compound, which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements. Another class has semipolar characteristics. Preferred classes of nonionic synthetic detergents are as follows:

1. A class of nonionic synthetic detergents under the tradename of "Pluronic". These compounds are formed by condensing ethylene oxide with a hydrophobic base formed by the condensation of propylene oxide with propylene glycol which is then "capped" by alkylating ($C_1$-$C_{18}$) or acylating ($C_2$-$C_{18}$) the molecule to form ether or ester groups. The hydrophobic portion of the molecule which, of course, exhibits water insolubility, has a molecular weight of from about 900 to 5,000. The addition of polyoxyethylene radicals to this hydrophobic portion tends to increase the water solubility of the molecule as a whole and the liquid character of the product is retained up to the point where the polyoxyethylene content is about 50% of the total weight of the condensation product.

2. The polyethylene oxide condensates of alkyl phenols, e.g., the condensation products of alkyl phenols having an alkyl group containing from about 6 to 12 carbon atoms in either a straight-chain or branched-chain configuration with ethylene oxide, the said ethylene oxide being present in amounts equal to 5 to 25 moles of ethylene oxide per mole of alkyl phenol. The condensates are "capped" as with group 1. The alkyl substituent in such compounds may be derived from polymerized propylene, diisobutylene, octene, or nonene, for example.

3. Those nonionic synthetic detergents derived from the condensation of ethylene oxide with the product resulting from the reaction of propylene oxide and ethylene diamine. The condensates are "capped" as in group 1. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000 are satisfactory.

4. The condensation product of aliphatic alcohols having from 8 to 22 carbon atoms, in either straight-chain or branched-chain configuration, with ethylene oxide, e.g., a coconut alcohol ethylene oxide condensate having from 5 to 40 moles of ethylene oxide per mole of coconut alcohol, the coconut alcohol fraction having from 10 to 14 carbon atoms.

Other preferred organic carriers include saturated fatty acids containing from 8 to 22 carbon atoms such as coconut fatty acid, lauric acid, cetic acid (also called cetylic), and stearic acid saturated acylate esters containing from about 10 to 80 carbon atoms wherein the fatty acyl group contains from 2 to about 18 carbon atoms and from 1 to about 3 carboxyl groups, and the alcohol group contains from 1 to about 18 carbon atoms and from 1 to about 6 hydroxy groups, e.g., methyl laurate, ethylene glycol dilaurate, dibutyl adipate, propylene glycol dimyristate and tristearin, mineral oil having a viscosity at 75° F. of from about 50 to about 700 Saybolt Seconds Furol (SSF), and saturated aliphatic hydrocarbons containing from about 10 to about 20 carbon atoms such as decane, 2-ethyldecane, tetradecane, isotetradecane, hexadecane and eicosane, as well as mixtures of said hydrocarbons.

Especially preferred organic carriers include mineral oil, saturated aliphatic hydrocarbons, diesters of propylene glycol and triesters of glycerine.

In an especially preferred embodiment of the invention a thickened form of the mineral oil or aliphatic hydrocarbon is used as the organic diluent, the thickening agent being selected from a group of specific types of organic waxes. These thickening agents have excellent compatibility with the peroxyacids and, when used in proper proportions with the mineral oil or hydrocarbons, are effective in producing a composition which has a viscosity within the range of normal toothpaste compositions, i.e., a Brookfield viscosity at 75° F. of from about 15 to about 100. Such composition can be spread from a squeezable tube onto a toothbrush and brushed upon the teeth in the conventional manner of toothpaste usage. The thickening agents are selected from the group consisting of:

1. saturated fatty acid triglycerides having melting points of from about 130° to about 250° F.

2. microcrystalline waxes having a melting point of from about 130° to about 250° F. and a penetration value of from about 0.5 to about 20 as determined by ASTM Test D-1321 and 3. polyethylene waxes having a melting point of from about 130° to about 250° F. and a penetration value of 77° F. of from about 0.5 to about 20 as determined by ASTM Test D-1321.

The amount of any particular thickening agent in these compositions is selected so as to produce the desired Brookfield viscosity. Generally a level of thickening agent within the range of from about 5% to about 30% by weight of the composition is used. Thus, these especially preferred compositions consist essentially of from about 2% to about 50% of the peroxyacid (preferably from about 5% to 35%), from about 5% to about 30% of a thickening agent selected from the types enumerated above, and the balance mineral oil or saturated aliphatic hydrocarbon, the specific amount of thickening agent being chosen so as to produce a Brookfield viscosity at 75° F. of from about 15 to about 100. The Brookfield viscosities quoted herein are determined on a Brookfield RVT ½ Heliopath Viscometer using an E spindle set at 2.5 rpm rotational speed.

Examples of Type 1 thickening agents are triglycerides such as myristic acid triglyceride, stearic acid triglyceride, and palmitic acid triglyceride. Mixtures of saturated fatty acid triglycerides such as those which make up hydrogenated tallow, hydrogenated soybean oil and hydrogenated cottonseed oil are also suitable.

Examples of Type 2 thickening agents are White Micro Wax (melting point 163°–169° F., penetration value (9) sold by International Wax Refining Company, Petrolite C-1035 (melting point 197°–202° F., penetration 4–5), Be Square 195 (melting point 193°–198° F., penetration 6–7), Ceramer 67 (melting point 200°–215° F., penetration 2.5–3.5) and Petrolite C-8500 (melting point 200°–210° F., penetration 4–7), all sold by Bareco Division of Petrolite Corporation.

Examples of Type 3 thickening agents are Polywax 655 (melting point 215° F., penetration 3.0), Polywax 500 (melting point 185° F., penetration 5.0) and Polywax E2020 (melting point 242° F., penetration 1.0), all sold by Bareco Division of Petrolite Corporation.

Inorganic carriers which can be present in the compositions of the invention include alkaline earth and alkali metal sulfates.

Desirable flavor ingredients which can be included in the concentrates are "saturated" esters such as ethyl butyrate, methyl acetate, and benzyl acetate; saturated ketones such as methyl amyl ketone, menthone, and eucalyptol.

Components of toothpastes, mouthwashes, lozenges, and chewing gums are disclosed in U.S. Pat. No. 4,472,373, to Ryan; in U.S. Pat. No. 4,083,955, to Grabenstetter et al.; and in U.S. Pat. No. 3,988,433, to Benedict, the disclosures of all of which are incorporated herein by reference.

Rinses, other than mouth rinses, of the present invention comprise water and/or compatible organic solvents (e.g., ethanol; isopropanol), a buffer (e.g., phosphate; citrate) capable of maintaining the pH of the rinse during use at pH of from about 5 to about 8, with from about pH=7.0 to about pH=7.5 preferred, and optionally other compatible components such as coloring (preferably less than about 0.2%), perfume (preferably less than about 2%), or detergents (described more fully above). The compatible components of the rinse are determined based on criteria similar to those used for choosing a carrier aobve in light of the use to be made of the rinse, e.g., a rinse to be used as a vaginal douche would contain compatible components safe for use in a vaginal douche (e.g., water, buffer), and a rinse to be used for acne would contain compatible components safe for use in rinsing the skin (e.g., water, buffer, detergent, perfume). The choice of compatible components for a rinse according to the present invention can be made without difficulty by one skilled in the art. Components of compositions for treating acne and for use as body scrubs are disclosed in U.S. Pat. No. 4,189,501, to Fulton, and in U.S. Pat. No. 4,350,681 to Fulton, the disclosures of both of which being incorporated herein by reference.

Creams and lotions of the present invention for treating or preventing topically-treatable anaerobe infections, such as acne, may contain compatible diluents that are safe for application to the tissue being treated. It is preferred that this carrier be an organic carrier as disclosed hereinabove, with this organic carrier constituting from about 0% to about 99.95% of the cream or lotion. It is further preferred that these creams or lotions be buffered, or contain a buffering system, capable of maintaining the pH of from about 5 to about 8, with from about pH=7.0 to about pH=7.5 preferred. Compatible detergents (as described more fully hereinabove) may constitute a part of the cream or lotion, preferably from about 0% to about 99.95% of the cream or lotion. Also, the cream of lotion may contain compatible coloring agents or perfumes.

The present invention further relates to a kit for making an aqueous mouth rinse of the present invention for use in treating or preventing disease of the oral cavity in humans or lower animals according to the method of treatment of the present invention. Because it is desirable, as noted hereinbefore, especially for chronic use, that the concentration of the mouth rinse of the present invention have an A.O. concentration generated by the monoperphthalic acid compound of less than about 1200 ppm, preferably less than about 300 ppm, the present invention provides a kit for facilitating the formulation of mouth rinses having the appropriate concentrations. Thus, the present invention provides a kit for making aqueous mouth rinses containing a monoperphthalic acid compound, preferably magnesium monoperphthalic acid, according to the present invention, for use in treating or preventing diseases of the oral cavity in humans or lower animals according to the method of treatment of the present invention, said kit comprising (a) a concentrate of the monoperphthalic acid compound, preferably a concentrate of magnesium monoperphthalic acid, and (b) a means for facilitating the desired dilution with water to produce a solution which has from about 30 ppm to about 1200 ppm, preferably from about 60 ppm to about 300 ppm, of available oxygen generated by the monoperphthalic acid compound.

By "concentrate of the monoperphthalic acid compound" as used herein is meant a concentrated composition of the monoperphthalic acid compound, preferably being magnesium monoperphthalic acid, that can be diluted with water to produce a mouth rinse according to the present invention. Thus, the concentrate of the monoperphthalic acid compound can comprise a monoperphthalic acid compound (preferably having the monoperphthalic acid compound being from about 1% to about 95% of the weight of the concentrate), plus adjunct components. It is preferred that these adjunct components include a buffer capable of buffering the aqueous solution to a pH of from about 5 to about 8, with from about pH=7.0 to about pH=7.5 most preferred, with said buffer preferably being from about 1% to about 75% of the weight of the concentrate. Preferred as a buffer are phosphate, and a carbonate/citrate mixture. Further preferred for use as adjunct components are sweetening and flavoring agents (preferably from about 0.1% to about 10% of the concentrate).

It is further preferred that the concentrate of the monoperphthalic acid compound be in solid form, preferably as a tablet or powder. When a solid concentrate is used in the kit of the present invention, it is preferred that the concentrate contain as an adjunct component a disintegrating agent to facilitate the dissoluton of the solid concentrate when the water is added. Preferred as the disintegrating agent is a mixture of carbonate and citrate. Other disintegrating agents and compositions are disclosed in European patent application No. 133,354, filed by Interox Chemicals Limited, and in U.S. Pat. Ser. No. 4,490,269, to Gallopo, the disclosures of both of which being incorporated herein by reference.

Nonlimiting, specific examples of means for facilitating the desired dilution of the above concentrates with water include a bottle prefilled with the concentrate, and a fill line marked on the bottle to ensure the proper quantity of water is added to achieve the desired dilution of the concentrate. Another example is a kit containing tablets of the concentrate, a cup marked with a fill line, and instructions (preferably printed on the side of the cup) indicating that one tablet is to be added to the cup and diluted with enough water to reach the fill line. Another example is a container marked with a solution fill line and a concentrate fill line, and instructions (preferably printed on the side of the container) indicating that first the powdered concentrate is to be added to reach the concentrate fill line, and second, enough water is to be added to this amount of concentrate to reach the solution fill line. Other means of facilitating the desired dilution of the concentrates are apparent to those skilled in the art.

EXAMPLE I

A mouth rinse according to the present invention may be prepared by dissolving a powdered mixture of 18 mg of magnesium monoperphthalate hexahydrate (84% active) and 85 mg of phosphate buffer (pH=7.2) in 15 ml of water, to give a 0.1% magnesium monoperphthalate mouth rinse. Similarly, a 0.5% magnesium monoperphthalate mouth rinse may be prepared by dissolving 90 mg of magnesium monoperphthalate hexahydrate (84% active) and 425 mg phosphate buffer (pH=7.2) in 15 ml of water.

Patients diagnosed as suffering from gingivitis are treated by rinsing with the above 0.5% mouth rinse for 30 seconds twice a day for a period of 3 weeks. This treatment results in an appreciable alleviation of the gingivitis, as well as a significant reduction in the number of pathogenic bacteria in dental plaque thereby resulting in further improved oral health. Similar results are obtained using the 0.1% mouth rinse.

Rinsing once a day for 30 seconds with either of the above described mouth rinses promotes continued gingival health in patients with healthy gingival tissue by significantly reducing the number of pathogenic bacteria in dental plaque.

EXAMPLE II

Mouth rinses according to the present invention may further be prepared as follows:

|  | Composition A (0.1%) | Composition B (0.5%) | Composition C (0.2%) |
|---|---|---|---|
| magnesium monoperphthalate | 18 mg | 90 mg | 36 mg |

|  | Composition A (0.1%) | Composition B (0.5%) | Composition C (0.2%) |
|---|---|---|---|
| hexahydrate (84% active) | | | |
| sodium carbonate | 25 mg | 116 mg | 50 mg |
| citric acid | 17 mg | 85 mg | 34 mg |

Dissolving Composition A, B or C in 15 ml of water (dissolving time about 1 minute) forms a mouth rinse (pH=7.2) according to the present invention containing 0.1% (A.O.=0.0065 w/v), 0.5% (A.O.=0.0325 w/v), and 0.2% (A.O.=0.0130 w/v) magnesium monoperphthalate, respectively.

Patients diagnosed as suffering from periodontal disease are treated by rinsing with the above 0.5% mouth rinse for 30 seconds three times a day for a period of 2 months. This treatment results in an appreciable alleviation of the periodontal disease, as well as a significant reduction in the number of pathogenic bacteria in dental plaque thereby resulting in further improved oral health. Similar results are obtained using the 0.1% or 0.2% mouth rinse.

Rinsing once a day for 30 seconds with either of the above described mouth rinses promotes continued gingival health in patients with healthy gingival tissue by significantly reducing the number of pathogenic bacteria in dental plaque.

A kit according to the present invention may be prepared by including within the kit a bottle of tablets of Composition A above, a cup marked with a fill line at a volume of 15 ml, and instructions printed on the outside of the cup which reads: "Add water to fill line; then add one tablet; let dissolve before use". Kits according to the present invention may similarly be made using tablets of Compositions B or C, above.

EXAMPLE III

A toothpaste or gel according to the present invention may be formulated as disclosed in U.S. Pat. No. 3,988,433, issued Oct. 26, 1976 to Benedict, the disclosures of which are incorporated herein by reference. Examples of formulations are:

| Composition A | |
|---|---|
| magnesium monoperphthalate | 5% |
| triacetin | balance |
| Composition B | |
| magnesium monoperphthalate | 2% |
| mineral oil (SSF-60) | balance |
| Composition C | |
| magnesium monoperphthalate | 10% |
| menthyl acetate and menthene (1:1) | 2% |
| sodium alkyl ($C_{10}$-$C_{12}$) sulfate | 4% |
| diethylether of polyethylene glycol (M.W.1000) | balance |
| Composition D | |
| Component I: | |
| magnesium monoperphthalate | 10% |
| potassium polyethyoxylated (4) | 4% |
| coconut fatty alcohol sulfate | |
| methyl laurate | balance |
| Component II: | |
| dicalcium orthophosphate | 40% |
| eucalyptol | 2% |
| phosphate buffer | 3% |
| NaF | 0.5% |
| color | 0.1% |
| methyl laurate | balance |

Toothpaste Composition D is formed upon mixing, by coextrusion from separate chambers of a toothpaste tube, components I and II in a 1:1 ratio just prior to use.

Patients diagnosed as suffering from gingivitis are treated by brushing with 1 ml (approximately 1 g.) of one of the above toothpastes or gels for 30 seconds three times a day for a period of 4 weeks. This treatment results in an appreciable alleviation of the gingivitis, as well as a significant reduction in the number of pathogenic bacteria in dental plaque thereby resulting in further improved oral health.

Brushing once a day for 30 seconds with any of the above described toothpastes or gels promotes continued gingival health in patients with healthy gingival tissue by significantly reducing the number of pathogenic bacteria in dental plaque.

EXAMPLE IV

A rinse according to the present invention may be prepared by dissolving a powdered mixture of 18 mg of magnesium monoperphthalate hexahydrate (84% active) and 85 mg of phosphate buffer (pH=7.2) in 15 ml of water, to give a 0.1% magnesium monoperphthalate rinse. Similarly, a 0.5% magnesium monoperphthalate rinse may be prepared by dissolving 90 mg of magnesium monoperphthalate hexahydrate (84% active) and 425 mg phosphate buffer (pH=7.2) in 15 ml of water. To either of these solutions is optionally added 0.5% of a perfume and/or 5% of a nonsoap anionic organic synthetic detergent, e.g., sodium lauryl sulphate.

Use of any of these solutions to wash the skin infected with acne (30 second washings, 3 times per day for two weeks) results in an appreciable alleviation of the acne. Washing one time each day for 30 seconds with any of these solutions promotes healthy skin by significantly reducing the number of pathogenic bacteria.

EXAMPLE V

A lotion for treating or preventing acne may be prepared by mixing (by weight) 1% magnesium monoperphthalate with 99% mineral oil. Application of this lotion to the skin infected with acne once a day results in an appreciable alleviation of the acne.

What is claimed is:

1. An aqueous mouth rinse composition comprising:
   (a) from about 0.05% to about 5% of a monoperphthalate compound having the general structure

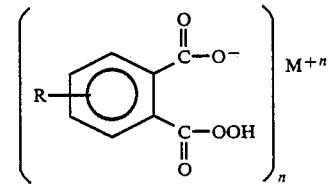

wherein $M^{+n}$ is a cation selected from the group consisting of an alkali metal, an alkaline earth metal, a non-toxic heavy metal, and trialkylammonium; and R is one or more substituents compatible with the peroxy acid functionality of the aromatic ring; and (b) a mouth rinse carrier comprising:
(1) from about 0.1% to about 10% of a flavoring agent;
(2) from about 0.1% to about 10% of a sweetening agent;
(3) from 0% to 20% of a humectant;
(4) from 0% to 2% of an emulsifying agent;
(5) from 0% to 60% ethanol; and
(6) the balance water.

2. An aqueous mouth rinse composition according to claim 1 wherein R is selected from the group consisting of hydrogen, substituted and unsubstituted saturated alkyl having from 1 to about 20 carbon atoms, substituted and unsubstituted aryl, substituted and unsubstituted benzyl, chloro, fluoro, nitro, sulphonate, trifluoromethyl, trialkylammonium, cyano, carboxy, carboxylate, percarboxylate, alkoxy, and combinations thereof.

3. An aqueous mouthrinse composition according to claim 2 wherein $M^{+n}$ is a divalent cation and the concentration of the monoperphthalate compound is from about 0.1% to about 2%.

4. An aqueous mouth rinse composition according to claim 2 wherein the monoperphthalate compound is magnesium monoperphthalate having the formula:

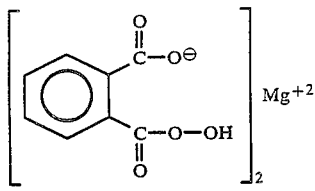

5. An aqueous mouth rinse composition according to claim 4 comprising:
(a) magnesium monoperphthalate acid in a concentration such that the available oxygen concentration generated by the magnesium monoperphthalate is from about 60 ppm to about 300 ppm;
(b) from about 0.1% (w/v) to about 10% (w/v) sweetening and flavoring agents;
(c) from about 0% to about 0.2% coloring agent;
(d) a buffer selected from the group consisting of phosphate, citrate, and citrate/carbonate; and said composition having a pH from about 5 to about 8.

6. An aqueous mouth rinse composition according to claim 5 wherein the pH is adjusted to from about 7.0 to about 7.5.

7. A toothpaste composition comprising:
(a) from about 0.1% to about 50% of a monoperphthalate compound having the formula

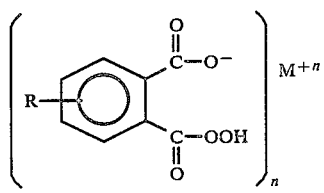

wherein $M^{+n}$ is a cation selected from the group consisting of an alkali metal, an alkaline earth metal, a non-toxic heavy metal, and trialkylammonium; and R is one or more substituents compatible with the peroxy acid functionality of the aromatic ring; and (b) a toothpaste carrier comprising:
(1) from about 0.1% to about 10% of a flavoring agent;
(2) from about 0.1% to about 10% of a sweetening agent;
(3) from 0% to 95% by weight of abrasives;
(4) from 0% to about 20% by weight of a sudsing agent;
(5) from 0% to about 10% by weight of a fluoride compound;
(6) from 0% to about 50% by weight of a thickening agent; and
(7) from 0% to about 70% of a humectant.

8. A toothpaste composition according to claim 7 in which R is selected from the group consisting of hydrogen, substituted and unsubstituted saturated alkyl having from 1 to about 20 carbon atoms, substituted and unsubstituted aryl, substituted and unsubstituted benzyl, chloro, fluoro, nitro, sulphonate, trifluoromethyl, trialkylammonium, cyano, carboxy, carboxylate, percarboxylate, alkoxy, and combinations thereof.

9. A toothpaste composition according to claim 8 wherein R is hydrogen, or the pharmaceutically-acceptable salts or esters of that compound.

10. A toothpaste composition according to claim 9 wherein the monoperphthalate acid compound is magnesium monoperphthalate, having the formula:

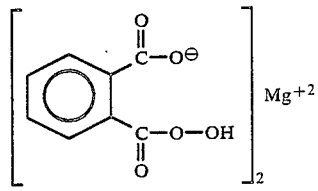

11. A toothpaste compositin according to claim 10 comprising:
(a) from about 1% to about 35% of magnesium monoperphthalate; and
(b) from about 65% to about 99% of a toothpaste carrier comprising:
(1) from 0% to about 100% of an organic carrier;
(2) from 0% to about 60% by weight of abrasives;
(3) from about 0.5% to about 10% by weight of a sudsing agent;
(4) from about 0.5% to about 5.0% by weight thickening agent;
(5) from 0% to about 36% of a humectant;
(6) from 0% to about 0.5% coloring agent; and
(7) from 0% to about 50% of a buffer capable of buffering the composition during use in the oral cavity to a pH of from about 5 to about 8.

12. A mouth spray composition comprising:
(a) from about 0.1% to about 25% of a monoperphthalate compound having the general structure:

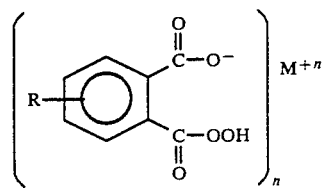

wherein $M^{+n}$ is a cation selected from the group consisting of an alkali metal, an alkaline earth metal, a non-toxic heavy metal, and trialkylammonium; and R is one or more substituents compatible with the peroxy acid functionality of the aromatic ring; and (b) a mouth spray carrier comprising:
(1) from about 0.1% to about 10% of a flavoring agent;
(2) from about 0.1% to about 10% of a sweeting agent;
(3) from 0% to 20% of a humectant;
(4) from 0% to 2% of an emulsifying agent;
(5) from 0% to 60% ethanol; and
(6) the balance water.

13. A mouth spray composition according to claim 12 wherein the mouth spray carrier is buffered such that the oral cavity during use of the mouth spray has a pH of from about 5 to about 8.

14. A mouth spray according to claim 12 wherein the monoperphthalate compound is magnesium monoperphthalate having the formula:

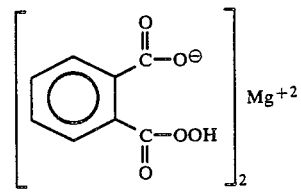

* * * * *

UNITED STATES PATENT AND TRADEMARK OFFICE
CERTIFICATE OF CORRECTION

PATENT NO. : 4,990,329
DATED : February 5, 1991
INVENTOR(S) : Padmini Sampathkumar It is certified that error appears in the above-identified patent and that said Letters Patent is hereby corrected as shown below:

Column 24, line 10, delete "0%" and insert therefor --0.5%--.

Column 24, line 46, delete "compositin" and insert therefor --composition--.

Column 24, line 53, insert after "an" and before "organic" the word --inert--.

Column 24, line 54, delete "0%" and insert therefor --0.5%--.

Column 25, line 21, delete "sweeting" and insert therefor --sweetening--.

Signed and Sealed this

Fifteenth Day of September, 1992

Attest:

DOUGLAS B. COMER

Attesting Officer

Acting Commissioner of Patents and Trademarks